United States Patent
Nadreau et al.

(10) Patent No.: US 8,400,621 B2
(45) Date of Patent: Mar. 19, 2013

(54) EGG EXAMINING DEVICE

(75) Inventors: Michael Nadreau, Landivisiau (FR);
Robert Croguennec, Milizac (FR)

(73) Assignee: Ceva Sante Animale, Lisbourne (FR)

( * ) Notice: Subject to any disclaimer, the term of this patent is extended or adjusted under 35 U.S.C. 154(b) by 467 days.

(21) Appl. No.: 12/087,262

(22) PCT Filed: Dec. 20, 2006

(86) PCT No.: PCT/FR2006/002815
§ 371 (c)(1),
(2), (4) Date: Jun. 5, 2009

(87) PCT Pub. No.: WO2007/077337
PCT Pub. Date: Jul. 12, 2007

(65) Prior Publication Data
US 2010/0141933 A1    Jun. 10, 2010

(30) Foreign Application Priority Data
Dec. 21, 2005 (FR) .................................... 05 12998

(51) Int. Cl.
*G01N 33/08* (2006.01)
*A01K 43/00* (2006.01)
(52) U.S. Cl. .......................................................... 356/53
(58) Field of Classification Search ............... 356/52–68; 119/6.8
See application file for complete search history.

(56) References Cited

U.S. PATENT DOCUMENTS

| 5,745,228 A * | 4/1998 | Hebrank et al. | 356/53 |
| 6,244,214 B1 * | 6/2001 | Hebrank | 119/6.8 |
| 7,573,566 B2 * | 8/2009 | Hebrank et al. | 356/53 |
| 2002/0075476 A1 | 6/2002 | Chalker, II et al. | |

FOREIGN PATENT DOCUMENTS

| FR | 2768517 | 3/1999 |
| JP | 06308098 | 11/1994 |
| WO | WO 99/01489 | 3/1999 |
| WO | WO 2004/023136 | 3/2004 |

OTHER PUBLICATIONS

Candling Eggs, Copyright © David Tippett 2000, retrieved from the internet: http://www.budgerigar.com.au/candling.html (4 pages).*
Terry A Tuxford, Editorial Feb. 2001, Plenty of Clear Eggs This Year? Who is the guilty party, the cock or the hen?, retrieved from the internet: http://bestofthebreeds.net/budgerigarworld/terry/ed0201.htm (3 pages).*
Internet Archive Wayback Machine, Candling Eggs, Copyright © David Tippett 2000, retrieved from the internet: http://www.budgerigar.com.au/candling.html (4 pages). Candling Eggs, Copyright © David Tippett 2000 was available on the internet on Jul. 11, 2001.*

* cited by examiner

*Primary Examiner* — Kara E Geisel
*Assistant Examiner* — Dominic J Bologna
(74) *Attorney, Agent, or Firm* — Pauly, Devries Smith & Deffner, L.L.C.

(57) ABSTRACT

The present invention relates to an automatic egg examining device for differentiating between fertilized eggs and unfertilized eggs, comprising emission means (3), which comprise, for each egg to be examined, at least one coherent laser source forming a coherent optical beam (31) directed at an egg (9) to be examined, reception means (4), which receive the light flux passing through the egg, and data processing means (7), which process the light flux received by said reception means in order to determine the state—fertilized or unfertilized—of the egg.

11 Claims, 2 Drawing Sheets

EGG EXAMINING DEVICE

CROSS REFERENCE TO RELATED-APPLICATIONS

This is a national stage of PCT/FR2006/002815 filed Dec. 20, 2006.

FIELD OF THE INVENTION

The present invention relates to an egg examining device for differentiating between fertilized and unfertilized eggs.

BACKGROUND OF THE INVENTION

In the poultry industry, in particular the chicken industry, automatic egg examining devices using the transparency of the egg in order to differentiate between fertilized and unfertilized eggs are known. These devices comprise emission means for emitting a light beam in the direction of an egg to be examined, receiving means for receiving the light beam passing through the egg, and means for processing data regarding the light beam received by said receiving means so as to determine the state of the egg. As a function of the level of absorption of the light beam passing through the egg, or the level of transparency of the egg, the data processing means can differentiate between fertilized eggs, i.e. eggs containing an embryo, and unfertilized eggs, including infertile eggs and rotten eggs. Some devices can also differentiate between live fertilized eggs containing a live embryo and dead fertilized eggs containing a dead embryo.

These examining devices conventionally comprise a despatch conveyor for transporting the eggs placed in their horizontal incubation racks or trays, emission means and receiving means being arranged on either side of the despatch conveyor. The emission means are generally constituted by emitters formed of light sources, such as filament lamps or light emitting diodes, conventionally of approximately 12 W, the receiving means being formed of photodiode-type receivers having receiving surface areas of approximately 0.5 mm². In order to obtain satisfactory transparency measurements, the emitters and receivers are arranged opposite one another in the same vertical plane.

The main drawback of said vertical examination systems is their low resistance to waste originating from the egg trays. The waste, such as bits of shell or the contents of broken eggs, feathers or other organic material, fall by means of gravity onto the emitters or receivers arranged below the trays which results in measurement variations and errors. In order to limit said measurement variations and errors, it is thus necessary for the examining device to be serviced on a very regular basis. Consequently, it has been suggested, in particular in patent document FR 2 768 517, to place a protective screen between the trays and the emitters arranged below said trays. The light beams from the emitters pass through the protective screen and automatic cleaning means are associated with said protective screen. Mechanical systems of this type are bulky and of complex design.

SUMMARY

The object of the present invention is to provide an examining device which overcomes the aforementioned drawbacks.

Consequently, the present invention relates to an automatic egg examining device for differentiating between fertilized and unfertilized eggs and optionally for differentiating between live fertilized eggs and dead fertilized eggs, comprising means for emitting a light beam in the direction of an egg to be examined, means for receiving the light beam passing through the egg and means for processing data regarding the light beam received by said receiving means so as to determine the fertilized or unfertilized state of the egg, characterised in that said emitting means comprise, for each egg to be examined, at least one coherent laser source forming a coherent optical beam in the direction of the egg.

The use of a coherent laser source according to the invention makes it possible to obtain a coherent optical beam which is fine and more concentrated and which penetrates the egg shell better than the light beam of a simple light emitting diode which means the light source does not necessarily have to be arranged on the side facing or exactly opposite the receiving means. The use of a coherent laser source therefore allows the light source and the receiving means to be arranged in many positions. According to the invention, it is therefore possible to arrange the light source in such a way that it is protected from waste which falls from the egg trays. The device according to the invention does not have to be serviced as often, is more stable and produces results which are more accurate.

According to one embodiment, said laser source is arranged below the eggs to be examined, the optical beam forming a non-null angle with respect to the vertical, for example between 5 and 45°, for example approximately 15°. Advantageously, said laser source is arranged below a protective plate. Since its beam is fine and coherent, the laser source may be arranged further away from the egg than the light sources of the prior art, without illuminating the adjacent eggs on the tray and with a non-null beam angle with respect to the vertical, in such a way that the laser source may be protected from waste, in particular below a protective plate.

According to another embodiment, said laser source is arranged above the eggs to be examined, the coherent beam forming a non-null angle with respect to the vertical, the measurements being advantageously taken when said optical beam reaches the bottom half of the egg.

The receiving means are advantageously arranged to the side of the vertical median plane of the egg opposite said laser source, preferably above the eggs to be examined.

In order to obtain a finer optical beam, said laser source is advantageously provided with focusing means for forming a concentrated coherent optical beam. According to one embodiment, said laser source is constituted by a laser diode preferably provided with a laser collimator forming said focusing means. Said laser source is advantageously an infrared laser source or a red laser source, preferably an infrared laser source.

According to one embodiment, said receiving means comprise, for each egg, at least one photo diode, preferably infrared, having a receiving surface area of at least 1 mm², preferably provided with means for focusing the light beam transmitted through the egg.

According to one embodiment, the examining device according to the invention comprises conveying means for transporting, preferably continuously, trays provided with wells in which the eggs to be examined are arranged, said emitting means comprising at least one row of coherent laser sources arranged transversely to the direction of movement of the trays for emitting at least one optical beam towards each of the eggs in a single row of a tray, and at least one row of receiving means for receiving the light beams coming from the eggs in a row of a tray.

According to one feature, the examining device further comprises measuring means for measuring the distance of the egg to be examined relative to the receiving means, the data regarding the light beam received by said receiving means being processed as a function of the distance measured so as to decrease the ray variations caused by the different heights of the eggs.

According to another feature, the examining device further comprises synchronisation means, such as an additional receiver for receiving ambient light waves and a timing device for synchronising the transparency measurements taken by the receiving means and the pulses of the laser source on the energy frequency of the ambient light waves, in the vicinity of the peak S of the time periods T of the energy of the ambient light waves. According to the invention, said synchronisation is a simple and cost-effective solution from a mechanical, electronic and optical point of view for providing immunity against the ambient light waves. Each transparency measurement comprises obtaining, in the vicinity of a peak S, a first value val1 corresponding to the level of light energy on the receiving means without the laser source associated therewith being activated, then obtaining a second value val2 corresponding to the level of light energy on the receiver with the laser source associated therewith activated, the transparency measurement being obtained by simply subtracting the first value val1 from the second value val2.

BRIEF DESCRIPTION OF THE FIGURES

The invention will be better understood and other objects, details, features and advantages will become more clear from the detailed explanatory description below of two, currently preferred, specific embodiments of the invention, with reference to the accompanying schematic drawings, in which.

DETAILED DESCRIPTION

Figure 1:
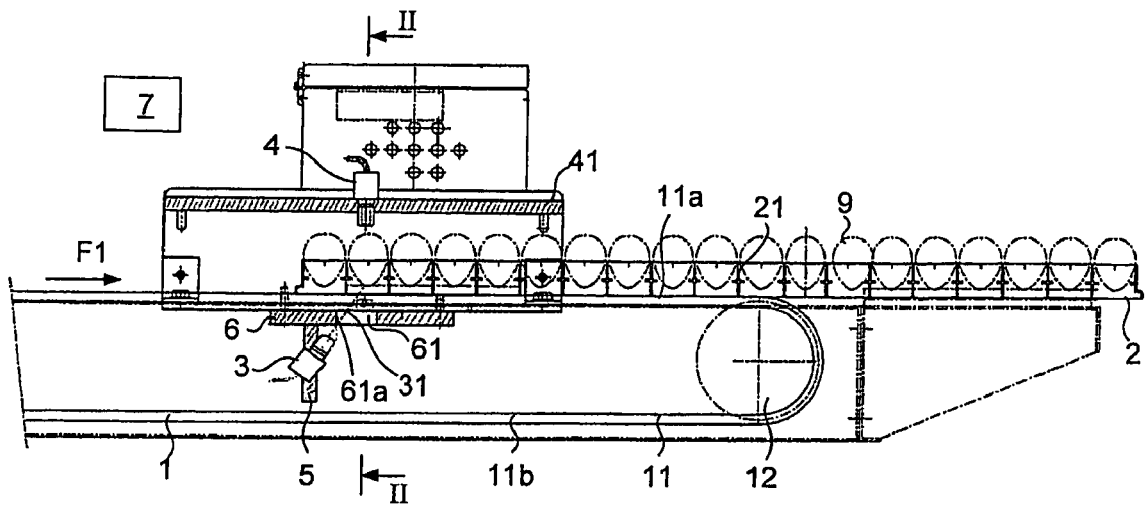
FIG. 1 is a longitudinal view, partly in cross-section, of an examining device according to a first embodiment of the invention.
Figure 2:
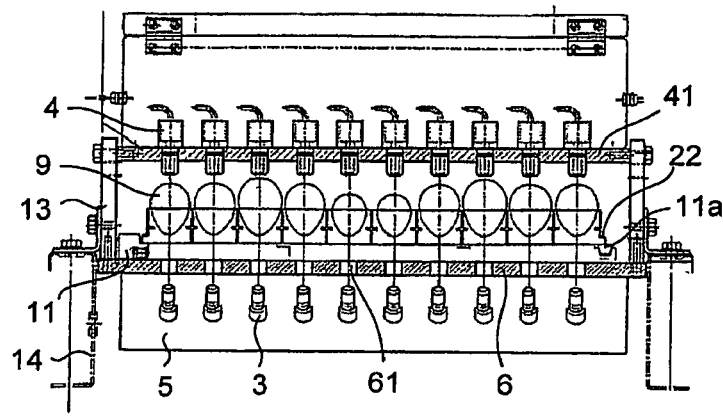
FIG. 2 is a transverse cross-section along line II-II of FIG. 1.

With reference to FIGS. 1 and 2, the device according to the invention comprises conveying means 1 for transporting incubation trays 2 of eggs along a conveying path, along which emission means or emitters 3 and receiving means or receivers 4 are arranged.

The conveying means 1 comprise an endless belt-type conveyor which transports the trays in the direction of movement F1. The conveyor is formed of two belts and two parallel chains 11 for synchronised transportation, each mounted in a looped manner on a preceding intermediate gear wheel and a following intermediate gear wheel 12. The spacing between the two chains is determined in such a way that the side edges 22 of the plates 2 abut the upper sides 11a of the two chains.

In the example shown, the device is configured for treating eggs 9 arranged on known "rectangular" trays 2 comprising parallel transverse rows of recesses or wells 21 which are open at the bottom, such as the incubation trays sold under the trade name "Petersime", the wells in the rows being longitudinally aligned.

The emitters and receivers are suitable for treating eggs in a single row. The device comprises, for each egg to be examined, an emitter 3 formed by a coherent laser source, preferably infrared, and an infrared receiver 4 for optically receiving the light beam passing through the egg.

The laser sources are arranged side by side on a ramp 5 formed by a vertical plate placed transversely to the direction of movement F1 under the upper edge 11a of the conveyor, for example between the lower edge 11b and the upper edge 11a. The laser sources, of which there are 10, are arranged on the ramp so as to be aligned with the 10 wells in each row of the trays travelling continuously above the ramp, each source being able to emit a light beam 31, forming a non-null angle with respect to the vertical, which illuminates a lower lateral side of each egg to be examined in order to take the measurement. The ramp is arranged below a horizontal protective plate 6 fixed beneath the upper edge and provided with a row of openings 61 for the beams to pass through. In the example shown, the ramp is fixed to the protective plate 6, before the openings 61 with respect to the direction of movement F1, said plate being fixed to a support structure 13 assembled on the frame 14 of the conveyor. The sources are longitudinally offset relative to the front end 61a of the openings, and are thus protected by the plate from possible waste falling from the eggs and/or the trays. The inclined coherent beam 31 of each laser source is directed so as to illuminate the bottom farthest side of the eggs to be examined by passing close to the front end 61a of an opening 61. In a variation, the openings are replaced with a single transverse slot.

The receivers 4 are mounted above the conveying path, side by side on a horizontal ramp 41 arranged transversely to the direction of movement. In the present example, the ramp 41 is formed by a plate mounted horizontally above the trays on the aforementioned support structure 13. The ramp carries a transverse row of 10 receivers, each receiver being arranged substantially vertically above an opening 61 in such a way that the receiver is substantially centred along the vertical median plane of an egg, whilst the point of impact of the optical beam 31 of the associated laser source is substantially at the lower end of the egg.

The receivers are connected to a control and data processing unit, indicated schematically with reference numeral 7, which determines, as a function of the intensity of the light beam detected by the receiver, whether an egg is fertilized or not. Advantageously, said data processing makes it possible to differentiate between live fertilized eggs, unfertilized eggs and dead fertilized eggs. The examining device according to the invention may be used to examine 18 day old eggs, i.e. eggs normally fertilized for 18 days, optionally to examine eggs between 6 and 10 days old, and is advantageously arranged before a device for removing unfertilized eggs and dead fertilized eggs from the trays and/or a device for injecting live fertilized eggs in the trays.

Each laser source 3 is advantageously constituted by an infrared laser diode provided with a laser collimator for further concentrating the light beam and generating a very fine optical beam. Since the coherent beam of the laser source penetrates the egg better than the light sources of the prior art, in particular better than a simple light emitting diode, the device is advantageously provided with laser sources which are weaker than the light sources of the prior art. By way of example, the device comprises laser diodes between 50 and 200 mW, for example 150 mW.

Each receiver 4 is constituted by a very sensitive photo diode having a receiving surface area of at least 1 mm$^2$, preferably between 2 and 15 mm$^2$, more preferably between 5 and 8 mm$^2$, for example approximately 7 mm$^2$. The photo diodes enable the measurements to be very linear and therefore very precise. Advantageously, each photo diode is provided with a focusing lens which makes it possible to focus the light beam so wrong information, such as reflections, is not measured.

Figure 3:
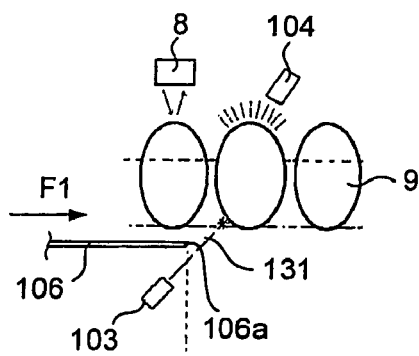
FIG. 3 is a schematic side view of an emitter and a receiver according to a variation of the first embodiment.

In a variation of the embodiment shown in FIG. 3, the receiver 104 is not centred relative to the measured egg. Each receiver is inclined with respect to the vertical and is longitudinally offset to the side of the vertical median plane of the egg which is opposite the associated laser source 103. In this variation, the laser sources 103 are arranged below a plate 106 having no openings, the laser sources simply being longitudinally offset with respect to the transverse edge 106a of the plate, the coherent beam 131 passing close to said transverse edge.

Using a coherent laser source makes it possible to avoid illuminating the adjacent eggs and the tray which surround the measured egg with the infrared ray, and thus avoids reflections on the eggs and the tray which would adversely affect the measurement taken. As is shown in FIG. 2, there may be significant variations in the size and shape of the eggs. Since the beam of the laser source is fine, variations in distance between the emitter and the egg can be minimised and therefore better stability of the transparency measurements to the variations in size and shape of the eggs is ensured.

Said variations in egg size also lead to variations in distance between the receiver and the egg. So as to minimise the measurement variations caused by said variations in distance, the device further comprises, with reference to FIG. 3, distance sensors 8, for example of the emitter/receiver type, arranged above the eggs to be examined and connected to the control and data processing unit. Each sensor measures the distance separating it from the top of the egg to be examined. The control and data processing unit 7 thus applies, as a function of the distance measured, an amplification coefficient on the signal sent by the receiver which represents the intensity of the light beam passing through the egg. The device comprises, for example, a transverse ramp of 10 distance sensors arranged above the trays and before the receivers for measuring the distances of the eggs in a single row.

Figure 4:
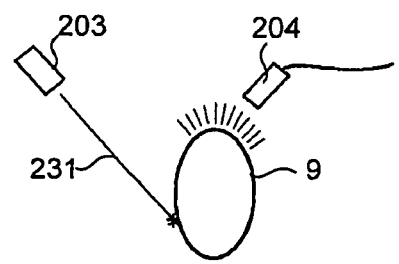
FIG. 4 is a schematic side view of an emitter and a receiver of an examining device according to a second embodiment of the invention.

FIG. 4 schematically shows a second embodiment in which the receivers 204 and the emitters 203 formed of coherent laser sources are arranged above the trays of eggs. The optical beam of each emitter 203 is inclined with respect to the vertical in such a way that, in order to take the measurement, the impact points of the coherent beam 231 on the shell of the egg to be examined during movement of said egg are arranged in the bottom half of the egg. The receivers are arranged similarly to those in FIG. 3, to the side of the vertical median plane of the eggs opposite the emitters. Since the angle between the coherent beam and the surface of the shell at the point of impact is smaller, the penetration coefficient of the beam is less significant than in the first embodiment shown in FIGS. 1 and 3. The line of impact points for taking the transparency measurement is arranged as low as possible in order to avoid reflections on the adjacent eggs and the tray, whilst maintaining a penetration coefficient which is sufficient to enable the transparency measurement.

In the examples described above, an egg is analysed using a receiver and an emitter. In variations, a plurality of receivers and/or emitters may be provided for analysing a single egg.

The device may also be configured for treating known offset incubation trays, in which the rows are arranged in a staggered manner, such as those sold under the trade name "Chickmaster". The laser sources and the receivers are thus arranged in a staggered manner on their respective ramp in two parallel transverse rows.

In order to reduce or eradicate transparency measurement errors caused by interference ambient light waves from artificial light sources, the transparency measurements taken by the receivers and the impulses of the laser sources are synchronised on the energy frequency of the ambient light waves.

Figure 5:
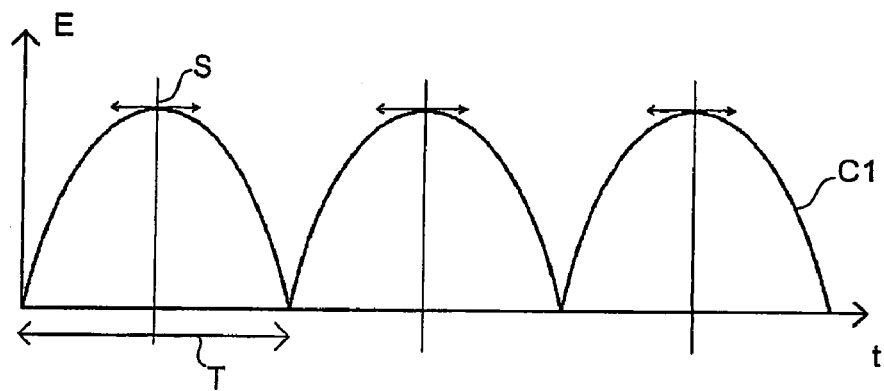
FIG. 5 is a graph showing the light energy coming from the ambient light sources as a function of time, before examination.

Before any examination procedure, the energy of the ambient light waves is measured. The curve C1 in FIG. 5 represents the light energy E as a function of time t of said ambient light waves. This measurement is taken by an additional receiver of the examining device and is sent to the control and data processing unit 7 in order to synchronise, for example by using a timer-type device, the transparency measurements and the impulses in the vicinity of the peak S of the time periods T of the energy of the ambient light waves, where the coefficient variation of the light energy, known as the leading coefficient, is lowest.

Figure 6:
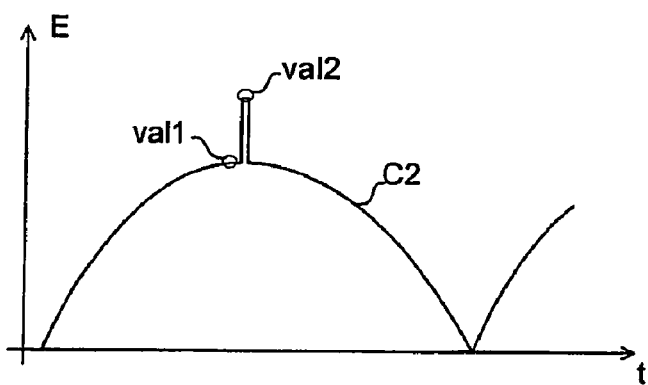
FIG. 6 is a graph showing the light energy coming from a laser source and ambient light sources as a function of time during examination; and, FIGS. 7 and 8 show different arrangements of laser sources on a ramp.

The curve C2 in FIG. 6 represents the light energy E as a function of the time t of the ambient light waves and a laser source during a transparency measurement. For each transparency measurement of an egg by a laser source/receiver pair, the control unit controls the receiver in order to obtain, in the vicinity of the peak S, a first value val1 corresponding to the level of light energy on the receiver without the laser source associated therewith being activated, and then to obtain a second value val2 corresponding to the level of light energy on the receiver with its associated laser source activated. The transparency measurement not influenced by the ambient light waves is thus obtained by subtracting the first value val1 from the second value val2. In order for the two values to be obtained in the shortest time possible and therefore to ensure that the two values are obtained in the vicinity of the peak, the command to emit the laser source is advantageously made by the associated receiver.

For each egg to be examined a plurality of successive transparency measurements are taken, for example 10, which are synchronised in the vicinity of the successive peaks S.

The transparency of eggs in the same row of a tray may be measured at the peak of the same time period of the energy of the ambient light sources. By way of example, in the case of 10 transparency measurements per egg, the transparency of the eggs is measured over the same 10 time periods T.

Figure 7:
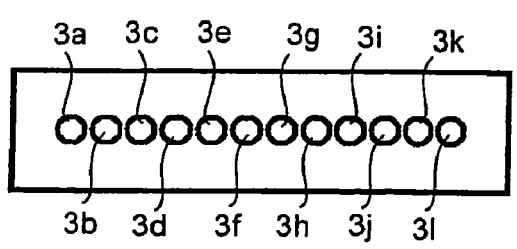
Figure 8:
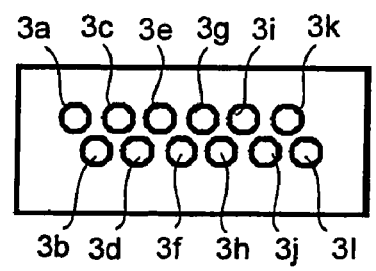

In order to avoid a disturbance between the receivers of different laser source/receiver pairs due to overlapping the light energies of the laser sources, the examining device applies a different command authorising a transparency measurement cycle for each emitter/receiver pair in such a way that only one laser source emits at a time. By way of example, in the case of a ramp of 12 laser sources identified by 3a to 3l and arranged in a row, as shown in FIG. 7, or arranged in a staggered manner in two rows, as shown in FIG. 8, the command to emit laser sources is as follows: a, g, b, h, c, i, d, j, e, k, f, l. The 12 laser sources can emit over the same time period of the energy of the ambient light waves, the first to emit therefore emitting slightly before its peak S and the last emitting slightly after its peak S.

Although the invention has been described together with specific embodiments, it is obvious that these are in no way limiting and that they include all technological equivalents of the means described and combinations thereof as long as these do not depart from the scope of the invention.

The invention claimed is:

1. An automatic egg examining device for differentiating between fertilized and unfertilized eggs, comprising means for emitting a light beam in the direction of an egg to be examined, means for receiving the light beam passing though the egg, and means for processing data regarding the light beam received by said receiving means in order to determine the fertilized or unfertilized state of the egg, characterised in that said emission means comprise, for each egg to be examined, at least one coherent laser source forming a coherent optical beam in the direction of the egg, wherein the device further comprises measuring means for measuring the distance of the egg to be examined relative to the receiving means, the data regarding the light beam received by said receiving means being processed as a function of the distance measured.

2. The examining device according to claim 1, characterised in that said laser source is arranged below the eggs, the optical beam forming a non-null angle with respect to the vertical.

3. The examining device according to claim 2, characterised in that said laser source is arranged below a protective plate.

4. The examining device according to claim 1, characterised in that said laser source is arranged above the eggs, the coherent beam forming a non-null angle with respect to the vertical.

5. The examining device according to claim 1, characterised in that the receiving means are arranged to the side of the vertical median plane of the egg opposite said light source, above the eggs to be examined.

6. The examining device according to claim 1, characterised in that said laser source is provided with focusing means for forming a concentrated optical beam.

7. The examining device according to claim 1, characterised in that said laser source is constituted by a diode laser provided with a laser collimator.

8. The examining device according to claim 1, characterised in that said laser source is an infrared laser source.

9. The examining device according to claim 1, characterised in that said receiving means comprise, for each egg, at least one photodiode, having a receiving surface area of at least 1 mm$^2$, provided with means for focusing the light beam passing through the egg.

10. The examining device according to claim 1, characterised in that it comprises conveying means for transporting trays provided with wells in which the eggs to be examined are arranged, said emission means comprising at least one row of coherent laser sources arranged transversely to the direction of movement of the trays so as to emit at least one optical beam towards each of the eggs in a single row of a tray, and at least one row of receiving means for receiving the light beams coming from the eggs in a row of a tray.

11. The examining device according to claim 1, characterised in that it further comprises synchronisation means for synchronising the transparency measurements taken by the receiving means and the pulses of the laser source on the energy frequency of the ambient light waves in the vicinity of the peak of the time periods of the energy of the ambient light waves.

* * * * *